United States Patent [19]

Busch et al.

[11] Patent Number: 6,110,918

[45] Date of Patent: Aug. 29, 2000

[54] MESYLATE TRIHYDRATE SALT OF 5-(2-(4-(1,2-BENZISOTHIAZOL-3-YL)-1-PIPERAZINYL)ETHYL)-6-CHLORO-1,3-DIHYDRO-2(1H)-INDOL-2-ONE (= ZIPRASIDONE), ITS PREPARATION AND ITS USE AS DOPAMINE D2 ANTAGONIST

[75] Inventors: Frank R. Busch, Gales Ferry; Carol A. Rose, Ledyard, both of Conn.

[73] Assignee: Pfizer Inc, New York, N.Y.

[21] Appl. No.: 09/180,456

[22] PCT Filed: Mar. 26, 1997

[86] PCT No.: PCT/IB97/00306

§ 371 Date: Mar. 2, 1999

§ 102(e) Date: Mar. 2, 1999

[87] PCT Pub. No.: WO97/42190

PCT Pub. Date: Nov. 13, 1997

Related U.S. Application Data

[60] Provisional application No. 60/016,537, May 7, 1996.

[51] Int. Cl.[7] .......................... A01N 43/60; A61K 31/495
[52] U.S. Cl. ............................................. 514/255; 544/360
[58] Field of Search .............................. 544/360; 514/255

[56] References Cited

U.S. PATENT DOCUMENTS 5,312,925  5/1994  Allen et al. .............................. 544/368

FOREIGN PATENT DOCUMENTS

| | | |
|---|---|---|
| 0281309A | 9/1988 | European Pat. Off. . |
| 281309 A1 | 9/1988 | European Pat. Off. . |
| 0281309B1 | 12/1991 | European Pat. Off. . |
| 0584903A | 3/1994 | European Pat. Off. . |
| 0586191A | 3/1994 | European Pat. Off. . |
| 584903 A1 | 3/1994 | European Pat. Off. . |
| 586191 A1 | 3/1994 | European Pat. Off. . |
| WO 95/00510 A1 | 1/1995 | WIPO . |
| WO9500510 | 1/1995 | WIPO . |

OTHER PUBLICATIONS

Howard et al., Journal of Medicinal Chemistry, vol. 39, No. 1, Jan. 5, 1996, pp. 143–148.

Howard H.R., et al., (1996) 3–Benzisothiazolylpiperazine Derivatives as Potential Atypical Antipsychotic Agents, Journal of Medicinal Chemistry, vol. 39, pp. 143–148.

*Primary Examiner*—Dwayne C. Jones
*Attorney, Agent, or Firm*—Peter C. Richardson; Paul H. Ginsburg; Kristina L. Konstas

[57] ABSTRACT

Mesylate Trihydrate Salt of 5-(2-(4-(1,2-benzisothiazol-3-yl)-1-piperazinyl)ethyl)-6-chloro-1,3-dihydro-2(1H)-indol-2-one (=Ziprasidone), Its Preparation and Its Use as Dopamine D2 Antagonist The invention relates to the mesylate trihydrate salt of 5-(2-(4-(1,2-benzisothiazol-3-yl)-1-piperazinyl)ethyl)-6-chloro-1,3-dihydro-2(1H)-indol-2-one ("ziprasidone mesylate trihydrate"), to pharmaceutical compositions containing ziprasidone mesylate trihydrate, and to methods of administering ziprasidone mesylate trihydrate to treat psychotic diseases.

7 Claims, 3 Drawing Sheets

TRIHYDRATE (large prism crystal)
1 cm = 55 μm

MESYLATE TRIHYDRATE SALT OF 5-(2-(4-(1,2-BENZISOTHIAZOL-3-YL)-1-PIPERAZINYL)ETHYL)-6-CHLORO-1,3-DIHYDRO-2(1H)-INDOL-2-ONE (= ZIPRASIDONE), ITS PREPARATION AND ITS USE AS DOPAMINE D2 ANTAGONIST

This application claims the benefit of U.S. Provisional Application Ser. No. 60/016,537, filed May 7, 1996.

BACKGROUND OF THE INVENTION

The invention is directed to the mesylate trihydrate salt of 5-(2-(4-(1,2-benzisothiazol-3-yl)-1-piperazinyl)ethyl)-6-chloro-1,3-dihydro-2H-indol-2-one (hereafter "ziprasidone mesylate trihydrate"), pharmaceutical compositions containing ziprasidone mesylate trihydrate, and methods of administering ziprasidone mesylate trihydrate to treat psychotic diseases. Ziprasidone is a potent psychotic agent and is therefore useful for treating various disorders including schizophrenia, migraine pain and anxiety. U.S. Pat. No. 5,312,925 refers to ziprasidone hydrochloride monohydrate, and states that ziprasidone hydrochloride monohydrate is substantially hygroscopically stable, which alleviates potential problems associated with weight changes of the active ingredient during the manufacture of capsules or tablets. U.S. Pat. No. 5,312,925 is herein incorporated by reference in its entirey. Ziprasidone hydrochloride monohydrate, however, has low aqueous solubility and, as a result, is more appropriate for capsule or tablet formulation than for injectable dosage forms.

Ziprasidone mesylate trihydrate also possesses hygroscopic stability. Ziprasidone mesylate trihydrate has the added advantage of having significantly greater aqueous solubility than the hydrochloride monohydrate, which makes the mesylate trihydrate more suitable for injectable dosage forms than the hydrochloride monohydrate. Further, of the four crystalline forms of ziprasidone mesylate, the mesylate trihydrate is the most thermodynamically stable in an aqueous medium at ambient conditions. This makes ziprasidone mesylate trihydrate advantageously suited for the preparation of consistent and precise dosage forms involving an aqueous medium.

BRIEF SUMMARY OF THE INVENTION

The present invention relates to the mesylate trihydrate salt of 5-(2-(4-(1,2-benzisothiazol-3-yl)-1-piperazinyl)ethyl)-6-chloro-1,3-dihydro-2H-indol-2-one.

This invention also relates to a pharmaceutical composition for the treatment of a psychotic disorder, such as schizophrenia, migraine pain or anxiety, comprising an amount of the mesylate trihydrate salt of 5-(2-(4-(1,2-benzisothiazol-3-yl)-1-piperazinyl)ethyl)-6-chloro-1,3-dihydro-2H-indol-2-one that is effective in treating said disorder, and a pharmaceutically acceptable carrier.

This invention also relates to a method of treating a psychotic disorder, such as schizophrenia, migraine pain or anxiety, in a mammal, including a human, comprising administering to said mammal an amount of the mesylate trihydrate salt of 5-(2-(4-(1,2-benzisothiazol-3-yl)-1-piperazinyl)ethyl)-6-chloro-1,3-dihydro-2H-indol-2-one that is effective in treating said disorder.

Table 1 below identifies selected peaks from the spectra of FIG. 1 by diffraction angle (two-theta), d-spacing, maximum intensity (max. int.), and relative intensity (rel. int.).

TABLE 1

X-RAY POWDER DIFFRACTION DATA FOR ZIPRASIDONE MESYLATE TRIHYDRATE

| Two-Theta (degrees) | D-spacing (degrees) | Max. Int. (counts/sec) | Rel. Int.(%) |
|---|---|---|---|
| 7.680 | 11.5025 | 84.00 | 8.54 |
| 9.657 | 9.1515 | 216.00 | 21.95 |
| 10.827 | 8.1650 | 48.00 | 4.88 |
| 12.205 | 7.2455 | 216.00 | 21.95 |
| 13.203 | 6.7002 | 803.00 | 81.61 |
| 13.564 | 6.5227 | 329.00 | 33.43 |
| 15.240 | 5.8089 | 191.00 | 19.41 |
| 15.507 | 5.7095 | 388.00 | 39.43 |
| 15.923 | 5.5612 | 836.00 | 84.96 |
| 16.680 | 5.3106 | 100.00 | 10.16 |
| 17.000 | 5.2112 | 103.00 | 10.47 |
| 17.946 | 4.9386 | 428.00 | 43.50 |
| 18.794 | 4.7178 | 383.00 | 38.92 |
| 19.881 | 4.4622 | 195.00 | 19.82 |
| 20.491 | 4.3306 | 93.00 | 9.45 |
| 21.585 | 4.1136 | 603.00 | 61.28 |
| 22.179 | 4.0047 | 984.00 | 100.00 |
| 23.472 | 3.7870 | 282.00 | 28.66 |
| 24.359 | 3.6511 | 240.00 | 24.39 |
| 24.918 | 3.5705 | 429.00 | 43.60 |
| 25.280 | 3.5201 | 159.00 | 16.16 |
| 26.034 | 3.4198 | 221.00 | 22.46 |
| 26.832 | 3.3199 | 196.00 | 19.92 |
| 27.594 | 3.2300 | 132.00 | 13.41 |
| 28.299 | 3.1511 | 261.00 | 26.52 |
| 29.151 | 3.0608 | 86.00 | 8.74 |
| 29.819 | 2.9938 | 197.00 | 20.02 |
| 30.361 | 2.9415 | 138.00 | 14.02 |
| 30.792 | 2.9014 | 112.00 | 11.38 |
| 32.448 | 2.7570 | 102.00 | 10.37 |
| 33.559 | 2.6682 | 73.00 | 7.42 |
| 34.264 | 2.6149 | 159.00 | 16.16 |
| 35.069 | 2.5567 | 165.00 | 16.77 |
| 35.742 | 2.5100 | 84.00 | 8.54 |
| 38.182 | 2.3551 | 158.00 | 16.06 |

DETAILED DESCRIPTION OF THE INVENTION

Figure 3:
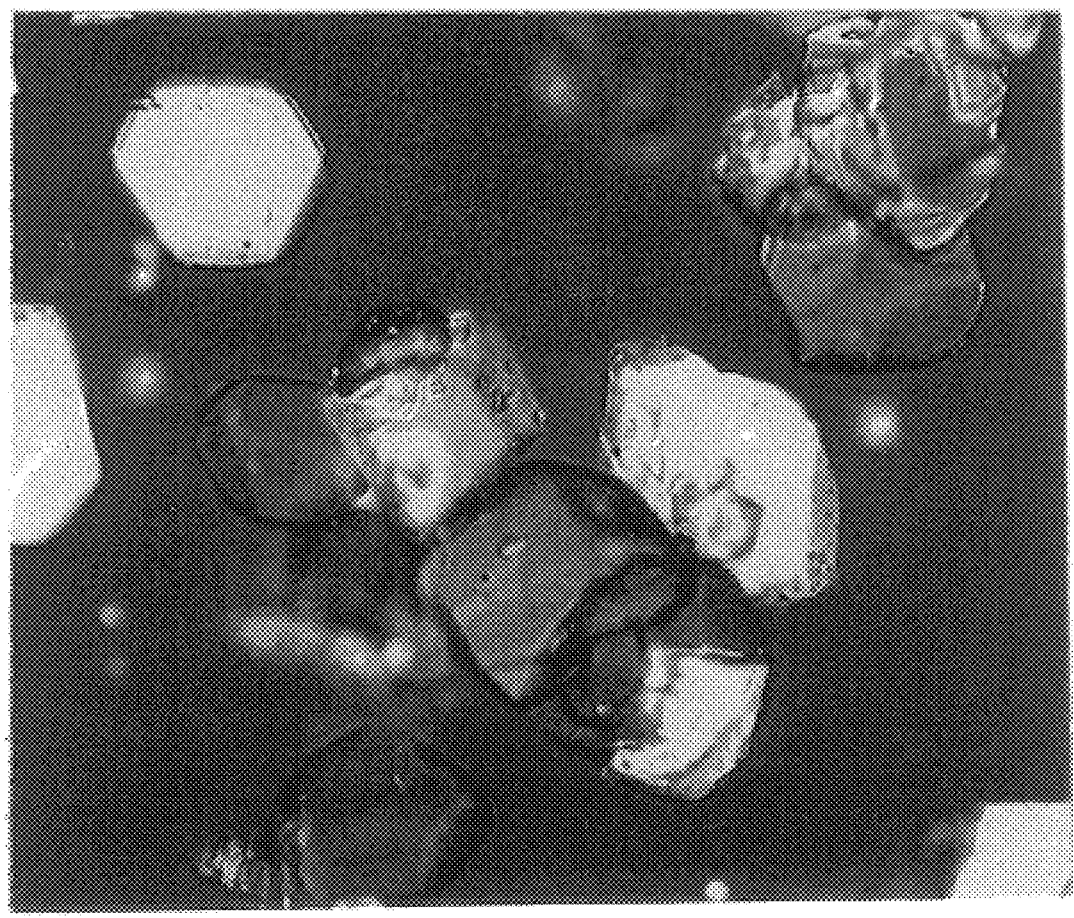
FIG. 3 shows a photomicrograph of ziprasidone mesylate trihydrate (prism crystals).

Ziprasidone mesylate exists in four distinct crystalline forms: ziprasidone mesylate anhydrous (lath crystal), ziprasidone mesylate dihydrate (lath crystal), ziprasidone mesylate dihydrate (needle crystal), and ziprasidone mesylate trihydrate (prism crystal). Each crystal form has distinct characteristics, such as a distinct powder X-ray diffraction pattern, a distinct single crystal X-ray, and a distinct crystal shape that can be observed by photomicrograph. The lath and needle crystals of ziprasidone mesylate dihydrate and the lath crystals of ziprasidone anhydrous are relatively long and thin in contrast to the prism crystals of ziprasidone mesylate trihydrate (FIG. 3). Ziprasidone mesylate anhydrous crystals are distinct, though similar in shape to the ziprasidone dihydrate lath crystals. The photomicrograph of FIG. 3 was obtained using an Olympus polarizing microscope (model BH-2) equiped with a halogen lamp, binocular eye piece, polarizing filter and Sony 3ccd video camera with Sony color printer.

Figure 1:
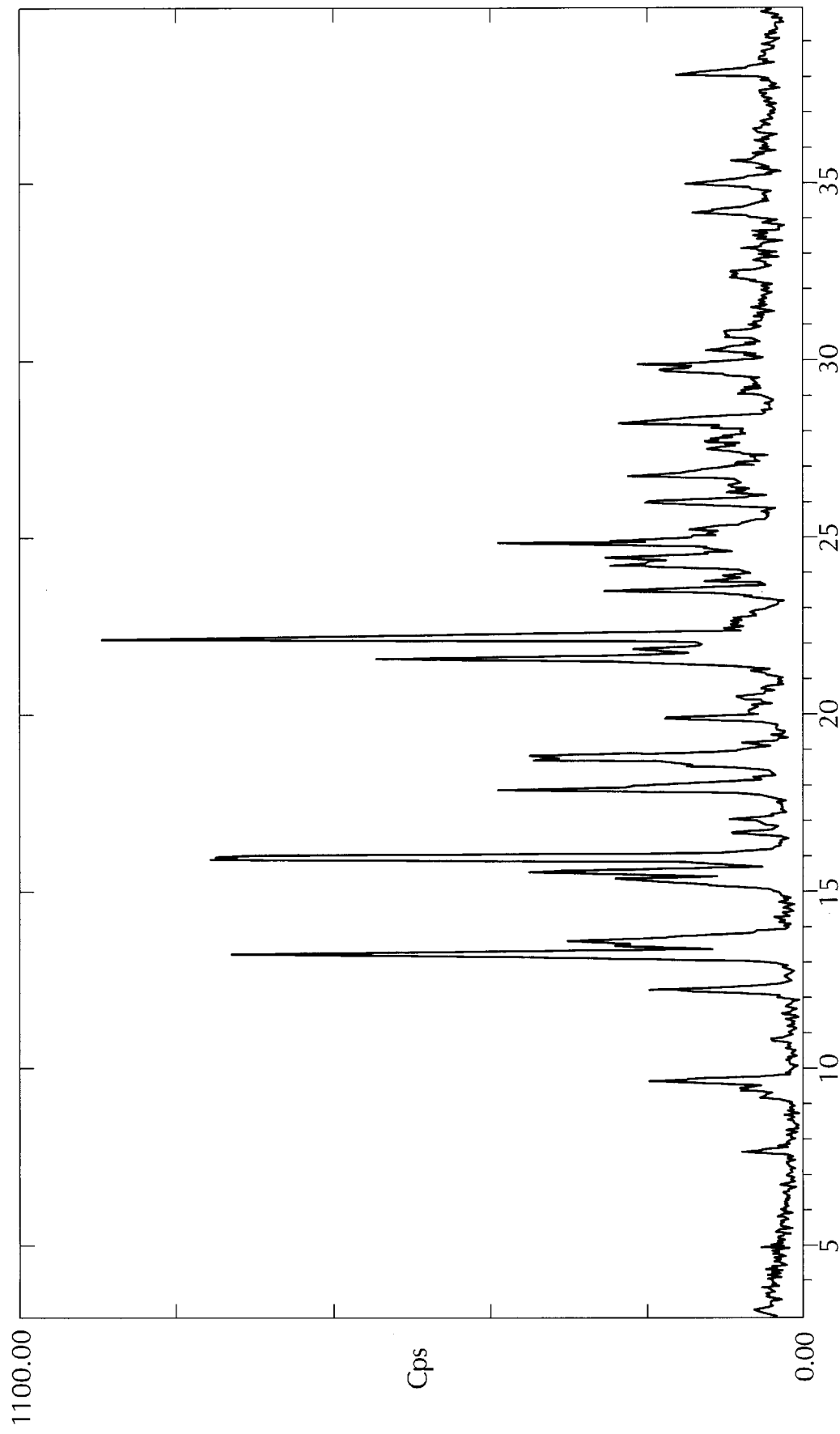
FIG. 1 depicts the X-ray powder diffraction spectrum of ziprasidone mesylate trihydrate expressed as intensity (Cps) versus diffraction angle (two-theta degrees).
Figure 2:
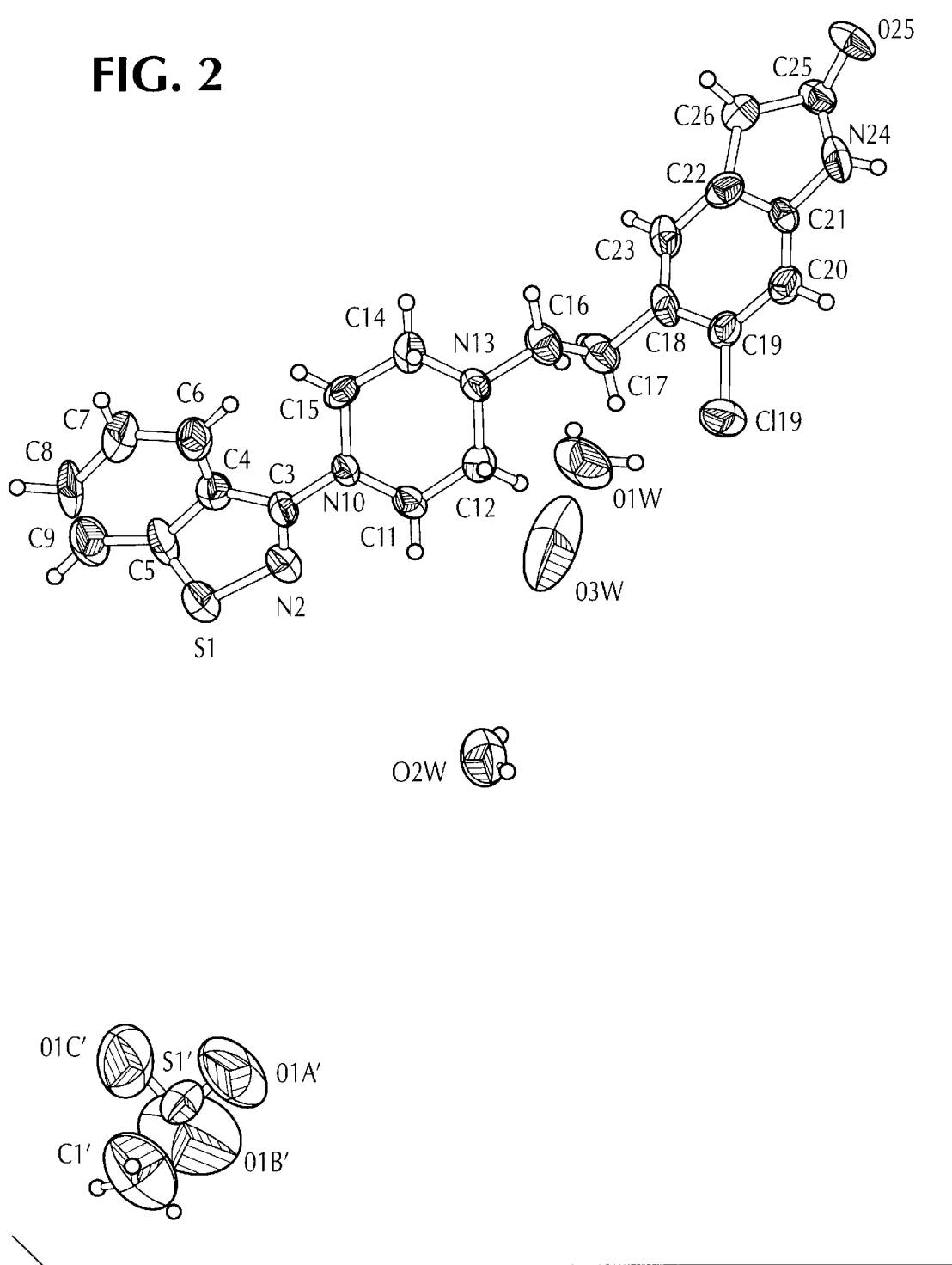
FIG. 2 depicts the structure of ziprasidone mesylate trihydrate as determined by single crystal X-ray crystallographic analysis.

The characteristic X-ray powder diffraction spectra of ziprasidone mesylate trihydrate is depicted in FIG. 1. The structure of ziprasidone mesylate trihydrate as determined by single crystal X-ray crystallographic analysis is depicted in FIG. 2. The X-ray powder diffraction spectra of FIG. 1 and the single crystal X-ray for FIG. 2 were taken on a Siemens R3RA/v diffractometer. Ziprasidone mesylate trihydrate is further characterized by its water content which is indicated by its Karl Fischer (KF) value of 9.6±1.0. The ziprasidone mesylate dihydrates (lath and needle) are the subject of co-pending United States provisional application entitled "Mesylate Dihydrate Salts of 5-(2-(4-(1,2-Benzisothiazol-3-yl)-1-piperazinyl)ethyl)-6-chloro-1,3-dihydro-2H-indol-2-one" (Pfizer docket number PC 9573), filed concurrently herewith. The foregoing co-pending United States provisional application is incorporated herein by reference in its entirety.

In an aqueous medium at ambient temperature, ziprasidone mesylate trihydrate is the most thermodynamically stable form of the four ziprasidone mesylate forms. As a result, the mesylate trihydrate is the preferred mesylate form for dosage forms involving an aqueous medium. In particular, the mesylate trihydrate is particularly suited for aqueous dosage forms for parenteral administration. The anhydrous mesylate form was found to be hygroscopic when exposed to air (humidity). This makes formulation of dosages difficult because the active ingredient changes in weight during the process of preparing the dosages. The relative thermodynamic stability of the three ziprasidone mesylate hydrated crystal forms was determined in a series of bridging experiments where mixtures of the crystal forms were allowed to equilibrate. For the bridging experiments, 200 mg samples were allowed to equilibrate in water (4 mL) at ambient temperature (22–25° C.). Two samples each of 90/10 (w/w) and 10/90 (w/w) mixtures of the two different identified polymorphs of ziprasidone mesylate (prism vs. dihydrate (lath), prism vs. dihydrate (needle), dihydrate (needle) vs. dihydrate (lath)) were evaluated. After equilibration (12–13 days), the solids were evaluated for polymorph changes and the supernatants were assayed by HPLC to determine solubility. It was found that the stability of the crystal forms to interconversion follows the trend observed for the solubility of the crystal forms, as shown in Table 2 below. Ziprasidone mesylate trihydrate was thermodynamically favored over the dihydrate forms.

Each of the four ziprasidone mesylate forms is significantly more soluble than ziprasidone hydrochloride monohydrate which has a solubility of 0.08 mg/ml in water at ambient temperature. The solubility of the four ziprasidone mesylate forms is indicated below in Table 2.

TABLE 2

Aqueous Solubility of Ziprasidone Mesylate Polymorphs

| POLYMORPH | SOLUBILITY IN WATER |
| --- | --- |
| trihydrate | 0.73 mg/mL |
| dihydrate (lath) | 1.11 mg/mL |
| dihydrate (needle) | 1.10 mg/mL |
| anhydrous | 1.27 mg/mL |

Ziprasidone mesylate trihydrate may be prepared from the free base (ziprasidone) which is prepared as described in column 4, lines 22–43 of U.S. Pat. No. 5,312,925, referred to above. The free base can also be prepared as described in U.S. Pat. No. 5,338,846, the disclosure of which is herein incorporated by reference in its entirety. When the intended use is as an injectable formulation, it is preferred to conduct the preparation under pyrogen-free and speck-free conditions. Speck-free solvents and reagents can be prepared by filtering them through a 0.45 μm Millipore® nylon filter.

Ziprasidone mesylate trihydrate is prepared by mixing the free base with a mixture of water and organic solvent, preferably tetrahydrofuran, at an organic solvent/water ratio (v/v) of about 3:7 to about 27:3 at a temperature ranging from 10° C. to 30° C., preferably ambient temperature (about 22–25° C.). Preferably, a THF/water ratio of 4:7.5 (v/v per unit of free base) is used. The mixture is then heated to a temperature of about 50° C. while stirring. A dilute solution of methanesulfonic acid is then prepared (1:4 w/w acid/water) to provide 1.2 equivalents acid, which is then added slowly, preferably over a 30 to 60 minute period, to the composition that includes the free base. The reaction mixture is then heated to reflux (about 65° C.) for about 30 minutes while protected from light. After the mixture has been heated, it is allowed to cool slowly to ambient temperature. While the mixture is cooling, ziprasidone mesylate trihydrate will begin to crystallize out of the mixture. Once the mixture has cooled to ambient temperature, it should be allowed to stir for at least another hour to ensure full crystallization. The trihydrate crystals will appear as large "yellowish" hexagonal prismatic crystals. The trihydrate crystals can be filtered from the composition through a poly-cloth filter, and then washed consecutively with appropriate volumes of a THF/water (65/35, v/v) solution and water. When allowed to dry at ambient temperature, the water content of the crystals has a Karl Fischer value ranging from 8.9–10.1% KF (theoretical KF for the trihydrate is 9.6%).

Ziprasidone mesylate trihydrate may be administered orally or parenterally, including intravenously or intramuscularly. For parenteral administration, it is preferred, where the use of water is called for, to use sterile water for injection (SWI). Administration through intramuscular injection is preferred. A preferred composition for intramuscular injection is ziprasidone mesylate trihydrate in combination with sulfoxybutyl β-cyclodextrin as carrier, preferably prepared at a ratio of 1:10 (w/w) trihydrate to carrier. Compositions containing ziprasidone mesylate trihydrate in combination with sulfoxy β-cyclodextrin can be prepared as described in co-pending United States provisional applications entitled "Method Of Making Inclusion Complexes" (Pfizer docket number PC 9563), filed concurrently herewith, and "Inclusion Complexes Of Aryl-Heterocyclic Compounds" (Pfizer docket number PC 8838), filed concurrently herewith. Both of the foregoing co-pending United States provisional applications are incorporated herein by reference in their entirety.

The effective dosage for ziprasidone mesylate trihydrate depends on the intended route of administration, the indication to be treated, and other factors such as age and weight of the subject. In the following dosage ranges, the term "mgA" refers milligrams of the free base (ziprasidone). A recommended range for oral dosing is 5–300 mgA/day, preferably 40–200 mgA/day, more preferably 40–80 mgA/day, in single or divided doses. A recommended range for parenteral adiministration, such as injection, is 2.5 mgA/day to 160 mgA/day, and preferably 5–80 mgA/day.

The present invention is illustrated by the following examples, but it is not limited to the details thereof. Unless otherwise indicated, the preparations described in the following examples were conducted under speck-free and pyrogen-free conditions. As used in the following examples, THF means tetrahydrofuran and SWI means sterile water for injection.

EXAMPLE 1

Purification of 5-[2-[4-(1,2-benzisothiazol-3-yl)-1-piperazinyl]ethyl]-6-chloro-1,3-dihydro-2H-indol-2-one To a clean and dry glass-lined tank, 46.8 kg of 5-[2-[4-(1,2-benzisothiazol-3-yl)-1-piperazinyl]ethyl]-6-chloro-1,3- dihydro-2H-indol-2-one and 2816.4 L of THF were charged. The slurry was heated to reflux and held for forty-five minutes to form a hazy solution. The solution was filtered through a 33-inch sparkler precoated with filter aid and backed with a Fulflo® filter (manufactured by Parker Hannifin Corp., Lebanon, Ind.) to a clean, dry glass-lined tank on a lower level. The filtered solution was concentrated by vacuum distillation, cooled to 5° C., and allowed to stir for two hours. The product was collected by filtration on a centrifuge and washed with cold (0–5° C.) THF. The product was collected and dried under vacuum at 450° C., to yield 40.5 kg of product. The product had a purity of 101.5% (within the typical range of 100±2% vs. the standard) as determined by an HPLC assay.

EXAMPLE 2

5-[2-[4-(1-benzisothiazol-3-yl)-1-piperazinyl]ethyl]-6-chloro-1,3-dihydro-2H-indol-2-one methanesulfonate trihydrate A slurry was produced by charging 1000 g of 5-[2-[4-(1,2-benzisothiazol-3-yl)-1-piperazinyl]ethyl]-6-chloro-1,3-dihydro-2H-indol-2-one, 7500 mL of SWI, and 4000 mL of THF to a 22-liter, three-neck, round-bottom flask equipped with a heating mantle, an overhead mechanical stirrer, a condenser, and a temperature probe. The flask contents were protected from light with an aluminum foil cover. The slurry was heated to 50° C. while stirring. Dilute methanesulfonic acid was prepared by combining 188 mL of methanesulfonic acid with 812 mL SWI. The dilute methanesulfonic acid was added slowly through a dropping funnel to the reaction mixture. The reaction was heated to reflux (about 65° C.), and a dark red solution formed as the reaction mixture was heated. The reaction mixture was allowed to stir under reflux conditions for approximately thirty minutes. After the thirty minute time period, the heating mantle was shut off to allow slow cooling of the reaction mixture with stirring. The reaction mixture was allowed to cool with stirring overnight (about 18 hours). As the reaction mixture cooled, the product crystallized out as large "yellowish" hexagonal prismatic crystals. The mixture was allowed to stir under ambient conditions for one hour. The product was isolated on a Buchner funnel with a poly cloth filter and was washed consecutively with 1500 mL of THF/SWI (65/35, v/v) and 1000 mL of SWI. The crystals were spread over glass trays and allowed to dry under ambient conditions to a Karl Fischer value of about 9.6%. The product was milled through a Mikro-Samplmill® (manufactured by the Pulverzing Machinery Division of Mikropul Corp., Summit, N.J.) equipped with a 0.027 H plate at a speed of 14,000 rpm. The yield was 945 g of product.

The product's structure was confirmed as 5-[2-[4-(1,2-benzisothiazol-3-yl)-1-piperazinyl]ethyl]-6-chloro-1,3-dihydro-2H-indol-2-one methanesulfonate trihydrate by NMR. $^{13}$C NMR (DMSO-d$_6$): δ 177.1(0), 163.0(0), 153.0 (0), 145.0(0), 132.4(0), 129.0(1), 127.8(0), 127.7(1), 127.1 (0), 126.5(0), 125.6(1), 124.9 91), 122.1(1), 110.6(1), 55.9 (2), 51.7(2), 47.5(2), 40.7(3), 36.2(2), 27.9(2). $^{1}$H NMR (DMSO-d$_6$): δ 10.5(s, 1H); 9.8(br. s, 1H); 8.2 (d, J=8.2 Hz, 1H); 8.1 (d, J=8.2 Hz, 1H); 7.6 (m, 1H), 7.5 (m, 1H); 7.3 (s, 1H), 6.9 (s, 1H); 4.2 (m, 2H); 3.7 (m, 2H); 3.5 (m, 2H), 3.4 (m, 2H); 3.1 (m, 2H); 2.4 (s, 3H).

Evaluation of the product by HPLC showed a peak with a retention time corresponding to that of a standard. The HPLC conditions are summarized in Table 3 below.

TABLE 3

| HPLC Conditions: | |
|---|---|
| Column: | Waters - Puresil C-18 15 cm length × 4.6 mm I.D. (Catalog No. WATO44345) |
| Mobile phase: | 0.05 M KH$_2$PO$_4$ pH 3.0: methanol (60:40. v/v) |
| Flow rate: | 2.0 mL/minute |
| Detection: | UV, 229 nm |
| Column temperature: | ambient |
| Sample Volume: | 10 µL |

EXAMPLE 3

5-[2-[4-(1,2-benzisothiazol-3-yl)-1-piperazinyl]ethyl]-6-chloro-1,3-dihydro-2H-indol-2-one methanesulfonate anhydrous A slurry was produced by charging 350 g of 5-[2-[4-(1,2-benziosothiazol-3-yl)-1-piperazinyl]ethyl]-6-chloro-1,3-dihydro-2H-indol-2-one and 7000 mL of isopropanol to a 12-liter three-neck, round-bottom flask equipped with a heating mantle, an overhead mechanical stirrer, a condenser, and a temperature probe. The slurry was heated to 50° C. while stirring. 65.9 mL of methanesulfonic acid was added slowly through a dropping funnel to the 50° C. reaction mixture. A slight exotherm to 55° C. along with thickening of the slurry and lightening of the slurry color were observed. The reaction was atmospherically distilled to remove 25% of the volume (1750 mL). The slurry was cooled to ambient temperature and allowed to stir overnight. The product was isolated on a sintered glass funnel and washed with fresh isopropanol. The solids were spread over glass trays and allowed to dry under ambient conditions to a Karl Fischer value of 0.5%. The yield was 420.3 g of product. Evaluation of the product by HPLC showed a peak with a retention time corresponding to that of a standard. The purity of the product, as determined by HPLC (conditions in Table 3), was 99.8%.

EXAMPLE 4

5-[2-[4-(1-benzisothiazol-3-yl)-1-piperazinyl]ethyl]-6-chloro-1,3-dihydro-2H-indol-2-one methanesulfonate dihydrate (needle crystals)

A slurry was produced by charging 5 g of 5-[2-[4-(1,2-benzisothiazol-3-yl)-1-piperazinyl]ethyl]-6-chloro-1,3-dihydro-2H-indol-2-one, 37.5 mL of water, and 20 mL of THF to a 150 mL, three-neck, round-bottom flask equipped with a heating mantle, an overhead mechanical stirrer, a condenser, and a temperature probe. The flask contents were protected from light with an aluminum foil cover. The slurry was heated to 65° C. with stirring. Dilute methanesulfonic acid was prepared by combining 1 mL of methanesulfonic acid with 4 mL SWI. The dilute methanesulfonic acid was added slowly through a dropping funnel to the reaction mixture. The reaction was heated to reflux (about 65° C.) and a dark red solution formed. The reaction mixture was allowed to stir under reflux conditions for approximately thirty minutes. After the thirty minute period, a seed crystal of the needle shaped polymorph was added to the reaction solution. Crystal formation started, and the heat was removed to allow slow cooling of the reaction with stirring. During cooling at 50° C., a thick "pinkish" slurry was observed in the flask. Water (20 mL) was added to the flask to thin the slurry. The product was allowed to stir under ambient conditions for one hour. The product was isolated on a Buchner funnel with a paper filter and the solids were allowed to dry under ambient conditions to a Karl Fischer value of about 6.6%. The yield was 6.03 g of product. The purity of the product, as determined by HPLC (conditions in Table 3), was 99.8%.

EXAMPLE 5

5-[2-[4-(1-benzisothiazol-3-yl)-1-piperazinyl]ethyl]-6-chloro-1,3-dihydro-2H-indol-2-one methanesulfonate dihydrate (lath crystals)

A slurry was produced by charging 25 g of 5-[2-[4-(1,2-benzisothiazol-3-yl)-1-piperazinyl]ethyl]-6-chloro-1,3-dihydro-2H-indol-2-one and 375 mL of water to a 500 mL, three-neck, round-bottom flask equipped with a heating mantle, an overhead mechanical stirrer, a condenser, and a temperature probe. The flask contents were protected from light with an aluminum foil cover. The slurry was heated to 50–55° C. while stirring. Methanesulfonic acid (5 mL) was added slowly through a dropping funnel to the reaction mixture. Thickening of the slurry and lightening of the slurry color were observed. The reaction was heated to reflux (about 100° C.) and allowed to stir for about one hour. The heat was removed to allow slow cooling of the reaction with stirring. The reaction solution was allowed to stir under ambient conditions for about one hour. The product was isolated on a Buchner funnel with a paper filter and the solids were allowed to dry under ambient conditions to a Karl Fischer value of about 6.2%. The yield was 32.11 g of product. The purity of the product, as determined by HPLC (conditions in Table 3), was 98.7%.

We claim:
1. 5-(2-(4-(1,2-benzisothiazol-3-yl)-1-piperazinyl)ethyl)-6-chloro-1,3-dihydro-2H-indol-2-one mesylate trihydrate.
2. A pharmaceutical composition for the treatment of a psychotic disorder comprising an amount of the compound of claim 1 that is effective in the treatment of said psychotic disorder and a pharmaceutically acceptable carrier.
3. A method of treating a psychotic disorder in a mammal comprising administering to said mammal an amount of the compound of claim 1 that is effective in the treatment of said psychotic disorder.
4. The method of claim 3 wherein said psychotic disorder is schizophrenia, migraine pain or anxiety.
5. The method of claim 3 wherein said pyschotic disorder is schizophrenia.
6. The method of claim 3 wherein said administration is parenteral administration.
7. The method of claim 6 wherein said parenteral administration is intramuscular injection.

* * * * *